United States Patent [19]

Blackburn et al.

[11] Patent Number: 4,935,400

[45] Date of Patent: Jun. 19, 1990

[54] REDUCTION OF HYDROCARBON LOSSES IN A MOLECULAR SIEVE HYDROCARBON TREATING SYSTEM

[75] Inventors: Glen A. Blackburn, Conroe, Tex.; Richard B. Macon, Woking, Surrey, England

[73] Assignee: Amoco Corporation, Chicago, Ill.

[21] Appl. No.: 256,688

[22] Filed: Oct. 12, 1988

[51] Int. Cl.$^5$ ............................................. B01J 38/04
[52] U.S. Cl. .................................. 502/517; 208/189; 208/150; 208/208 R; 208/310 Z; 208/301; 208/305; 502/34; 502/514
[58] Field of Search .................. 208/189, 150; 502/34, 502/514, 517

[56] References Cited

U.S. PATENT DOCUMENTS

| | | | |
|---|---|---|---|
| 3,188,293 | 6/1965 | Bacon et al. | 502/34 |
| 3,288,719 | 11/1966 | Asher et al. | 502/34 |
| 3,392,111 | 7/1968 | Napier et al. | 208/189 |
| 3,408,286 | 10/1968 | Hepp | 208/150 |
| 3,472,786 | 10/1969 | Urban et al. | 502/34 |
| 3,849,295 | 11/1974 | Addison | 208/150 |
| 4,179,399 | 12/1979 | Lichtenberger et al. | 502/517 |

Primary Examiner—Helane Myers
Attorney, Agent, or Firm—L. W. White; F. E. Hook

[57] ABSTRACT

Molecular sieves are used to remove sulfur compounds (e.g., COS and $H_2S$) from liquid hydrocarbon streams, particularly liquid propane. During regeneration of the sieves, some of the liquid hydrocarbons remains on the sieves and is lost by vaporization during the purge step and the liquid fill step. This invention reduces the loss by recovery and recycle of the vaporized hydrocarbons in the liquid recovery process.

1 Claim, 6 Drawing Sheets

FIG. 1

TREATING CYCLE

▼ – VALVE CLOSED
▽ – VALVE OPEN

FIG. 2

DRAIN CYCLE

▼ – VALVE CLOSED
▽ – VALVE OPEN

FILL CYCLE

▼ – VALVE CLOSED
▽ – VALVE OPEN

REDUCTION OF HYDROCARBON LOSSES IN A MOLECULAR SIEVE HYDROCARBON TREATING SYSTEM

BACKGROUND OF THE INVENTION

1. Field of the Invention

This invention pertains to a method of recovering liquid hydrocarbons from a molecular sieve sorbent bed in a hydrocarbon treating system. This invention is particularly useful in recovering "sponge" or "sponged" propane that has been retained by a bed of zeolitic molecular sieves in a treatment system designed to remove sulfur compounds (e.g., carbonyl sulfide) from liquid propane.

2. Description of the Prior Art

Various methods have been used to remove sulfur compounds (e.g., carbonyl sulfide (COS), carbon disulfide ($CS_2$), hydrogen sulfide ($H_2S$), and the like) from hydrocarbon streams. Such methods have been referred to as "sweetening" or "desulfurization" processes.

The reasons for removing sulfur compounds from hydrocarbon streams are almost as diverse as the sweetening methods used. Two of the primary reasons are (a) to protect the environment by eliminating or reducing the amount of noxious/toxic hydrogen sulfide and/or sulfur dioxide formed during combustion, and (b) to protect hydrocarbon process equipment that comes in contact with such hydrocarbon streams. Sulfur compounds, particularly $H_2S$, are known to corrode base metals (metal parts) and to foul catalysts used in refineries.

The specification limits upon the maximum amount of sulfur compounds that may be present in a particular hydrocarbon product will vary depending upon the product and its conventional use. Increasingly stringent limits have been placed on liquid hydrocarbons conventionally used as fuels or fuel additives. E.g., gasoline and diesel fuels in the transportation area, and liquid propane and butane fuels in combustion heating.

One method that has been used to sweeten liquid hydrocarbons involves contacting the liquid hydrocarbon stream with one or more sorbent beds loaded with materials that sorb the sulfur compound(s) as the hydrocarbon stream passes through the bed. Various sorbents have been used, but molecular sieves have been particularly useful in this application. The molecular sieves are typically zeolitic materials, both natural and synthetic, comprising ordered porous crystalline aluminosilicates having a definite crystalline structure, as determined by X-ray diffraction within which there are a large number of small cavities, which are interconnected by a series of still smaller channels or pores having a uniform pore size or pore size distribution in a rigid three-dimensional matrix of $SiO_4$ and $AlO_4$. Such molecular sieves and the methods of making and using them in sweetening hydrocarbon streams are well known, as illustrated by the following nonexhaustive list of patents:

| Assigned to Union Carbide | | Others | |
|---|---|---|---|
| U.S. Pat. Nos. | | | |
| 3,069,362 | 4,645,516 | 3,051,646 | 4,313,821 |
| 3,069,363 | 4,683,217 | 3,102,855 | 4,404,118 |
| 3,211,644 | 4,684,511 | 3,188,293 | 4,540,842 |
| 3,620,969 | 4,684,617 | 3,218,250 | 4,703,025 |
| 3,654,144 | 4,686,029 | 3,282,831 | |
| 3,660,967 | 4,686,092 | 3,450,629 | |
| 4,098,684 | 4,686,093 | 3,490,865 | |
| | 4,738,837 | | |

The disclosures of these patents are incorporated herein by reference to the extent that any such patent, or combination of patents, describes a molecular sieve, or a method of making a molecular sieve, that can be used to remove sulfur compounds from a liquid hydrocarbon stream. As these patents indicate, the zeolitic materials can be manufactured with a uniform pore size and with a pore size chosen to selectively adsorb molecules of certain dimensions (e.g., COS) while rejecting molecules of larger dimensions (e.g., propane) —hence, the term "molecular sieve."

Under conditions of use in sweetening operations, a sour stream of liquid hydrocarbons is contacted with the molecular sieves under conditions sufficient to remove appreciable quantities of the sulfur compound(s) from the hydrocarbon stream. Typically, a pressurized hydrocarbon stream is passed through one or more "packed columns" or "beds" of molecular sieves at a flow rate and other process conditions that provides adequate contact time for the sulfur compounds to be removed. As the molecular sieves reach the limit of their capacity to sorb the sulfur compounds (i.e., the molecular sieves become "loaded") and prior to "breakthrough" when the treated hydrocarbon product passing through the molecular sieves fails to meet specifications with respect to the amount of sulfur compounds in the product, the flow of the hydrocarbon is stopped until the bed of molecular sieves can be regenerated, or more typically, the flow is diverted to another bed of molecular sieves while the first bed is regenerated.

The bed of molecular sieves that is loaded with sorbed sulfur species can be regenerated by draining liquid hydrocarbon from the bed and then heating the bed of molecular sieves under conditions sufficient to volatilize and desorb the sulfur species and thereby reactivate the molecular sieves to further sorption. The vapors from the heated bed are typically flared. This technique for regeneration is well known and widely used in the industry. Unfortunately, this technique results in a substantial loss of hydrocarbon product, i.e., material that does not drain from the bed and is lost to the flares when the bed is heated. The loss of product retained by the molecular sieves (sometimes referred to as "sponge" or "sponged" hydrocarbon) is exacerbated when the sulfur content in the hydrocarbon feed stream is high and/or when the specification on the treated product is stringent. In such instances, the bed must be regenerated more frequently.

A method has now been discovered that will reduce this loss of hydrocarbon and thereby enhance the economics of the treatment process.

SUMMARY OF THE INVENTION

The novel sweetening process comprises the steps (a) stopping the flow of sour liquid hydrocarbon to a bed of molecular sieves in a hydrocarbon sweetening plant, (b) draining liquid hydrocarbon from the bed of molecular sieves, (c) purging the bed with a heated gaseous hydrocarbon until substantial amounts of sponged hydrocarbon has been removed from the bed and reintroducing the hydrocarbon/sponged hydrocarbon stream into the hydrocarbon recovery portion of the plant upstream of the on line molecular sieve bed, (d) regenerating the purged bed by contact with a gaseous hydrocarbon heated to a temperature sufficient to volatilize and desorb sulfur species from the molecular sieves, (e) cooling the regenerated bed by contact with hydrocarbon residue gas or sweetened hydrocarbon, (f) refilling the bed with sweetened liquid hydrocarbon, and (g) continuing the sweetening process by starting the flow of sour liquid hydrocarbon through the freshly regenerated bed.

The novel process is particularly useful when the liquid hydrocarbon is propane or butane.

BRIEF DESCRIPTION OF THE DRAWINGS

FIGS. 1–6 cover the same physical embodiment of the plant, but the valving/gas flow, etc. are changed to represent the various steps of the process.

DETAILED DESCRIPTION OF THE DRAWINGS

Figure 1:
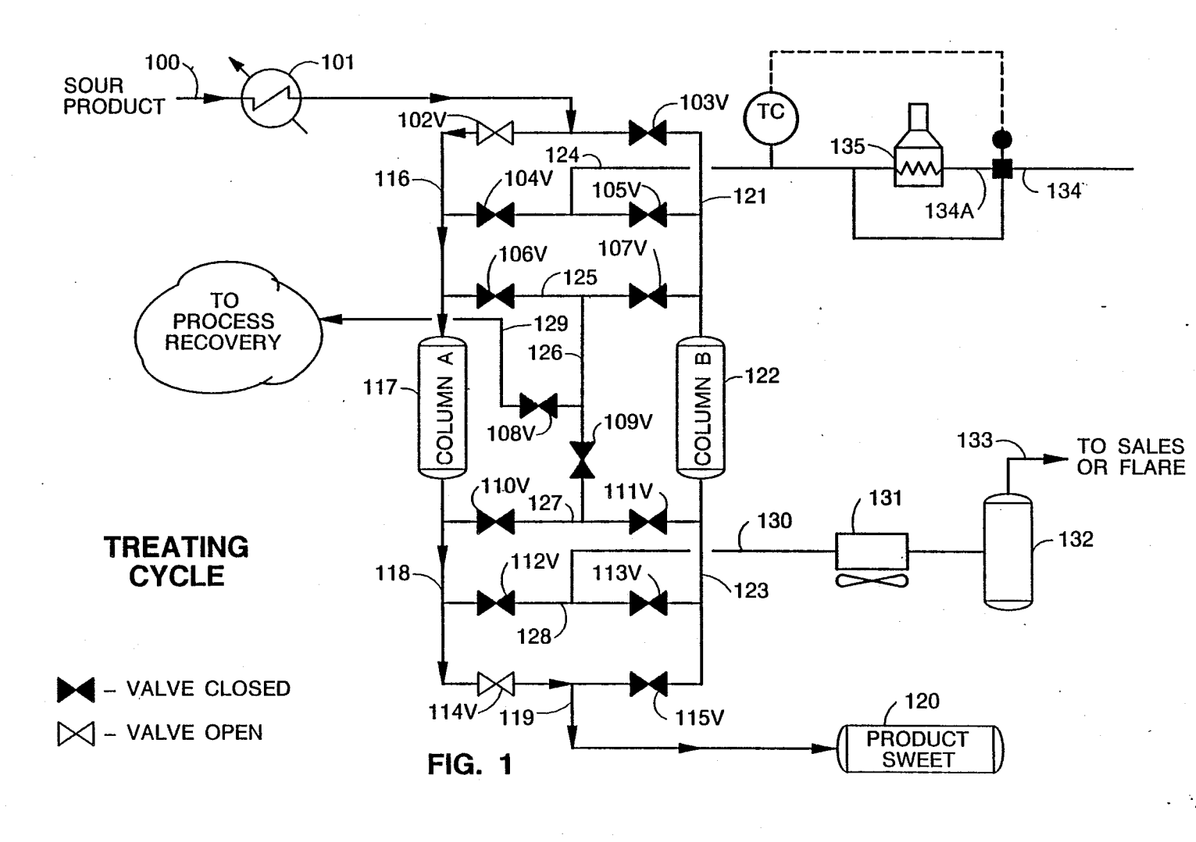
FIGS. 1 through 6 are schematics of a portion of a hydrocarbon processing plant in which a sour crude hydrocarbon has been separated into different components or "cuts" or "fractions", and one cut is being sweetened by contact with molecular sieves in columns A and B. The loaded beds are regenerated and sponged hydrocarbon product recovered according to the present invention.

FIG. 1: The sour product flows through line 100 into a heat exchange 101, where it is cooled, and into Column A (117) by way of line 116. Column A and Column B are packed with molecular sieves which sorb sulfur species in the sour product. The sweetened product thus flows from Column A to a collection point (120) through lines 118 and 119. This represents the treatment cycle with Column A on adsorption.

Figure 2:
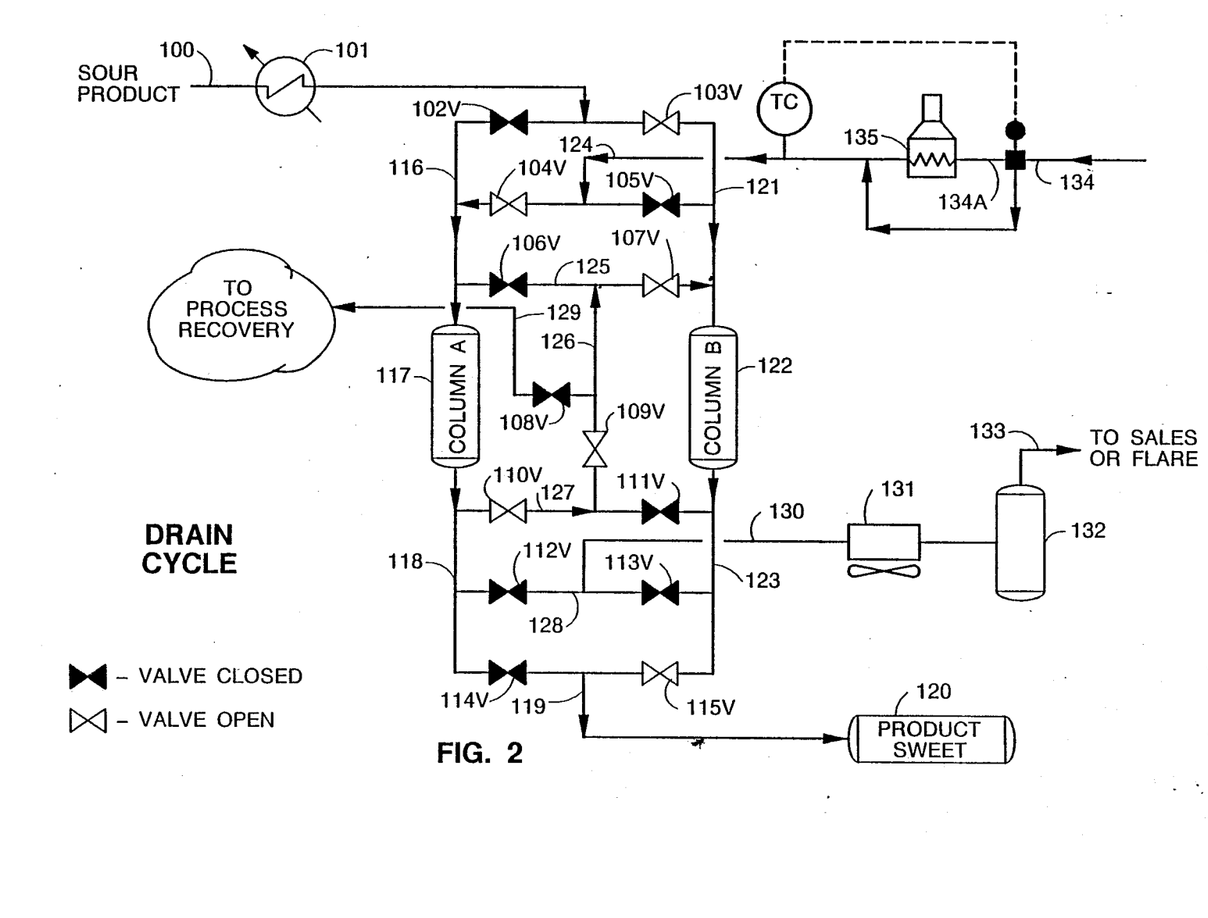

FIG. 2: The flow of sour product to Column A is diverted to Column B by changing the valving as shown in FIG. 2. In addition, the liquid product is drained from Column A by the pressure created when the bed is heated (e.g., by residue gas flowing through feed lines 134, 124 and 116 (or 121) into the column being drained) to a temperature above the boiling point of the sponged hydrocarbon; the liquid product is thereby flowed through line 126 into Column B along with sour product for further treatment in Column B.

Figure 3:
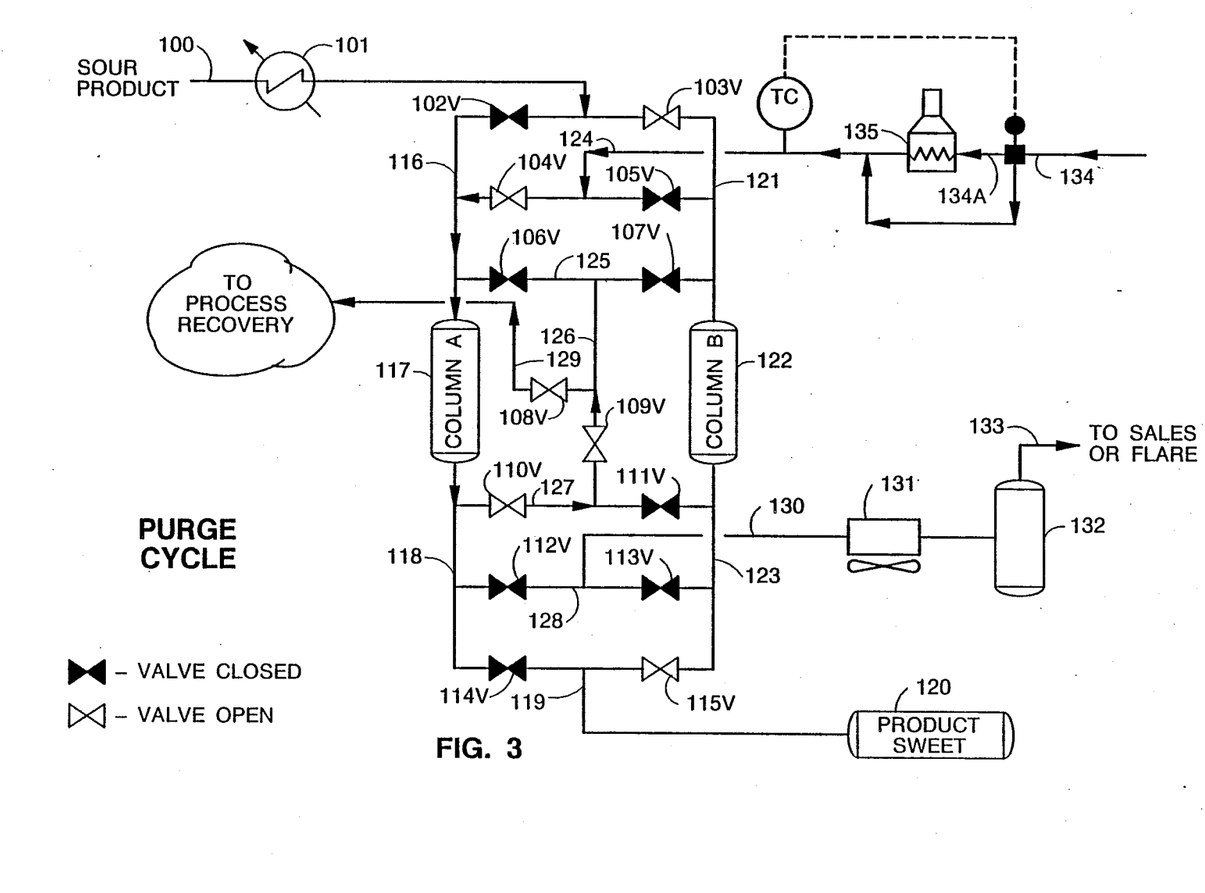

FIG. 3: Once the majority of liquid product has been drained from Column A, the remaining sponged product is purged from the molecular sieves by flowing heated purge gas through line 134/Column A back to the front end of the plant for further process recovery of the vaporous effluent.

Figure 4:
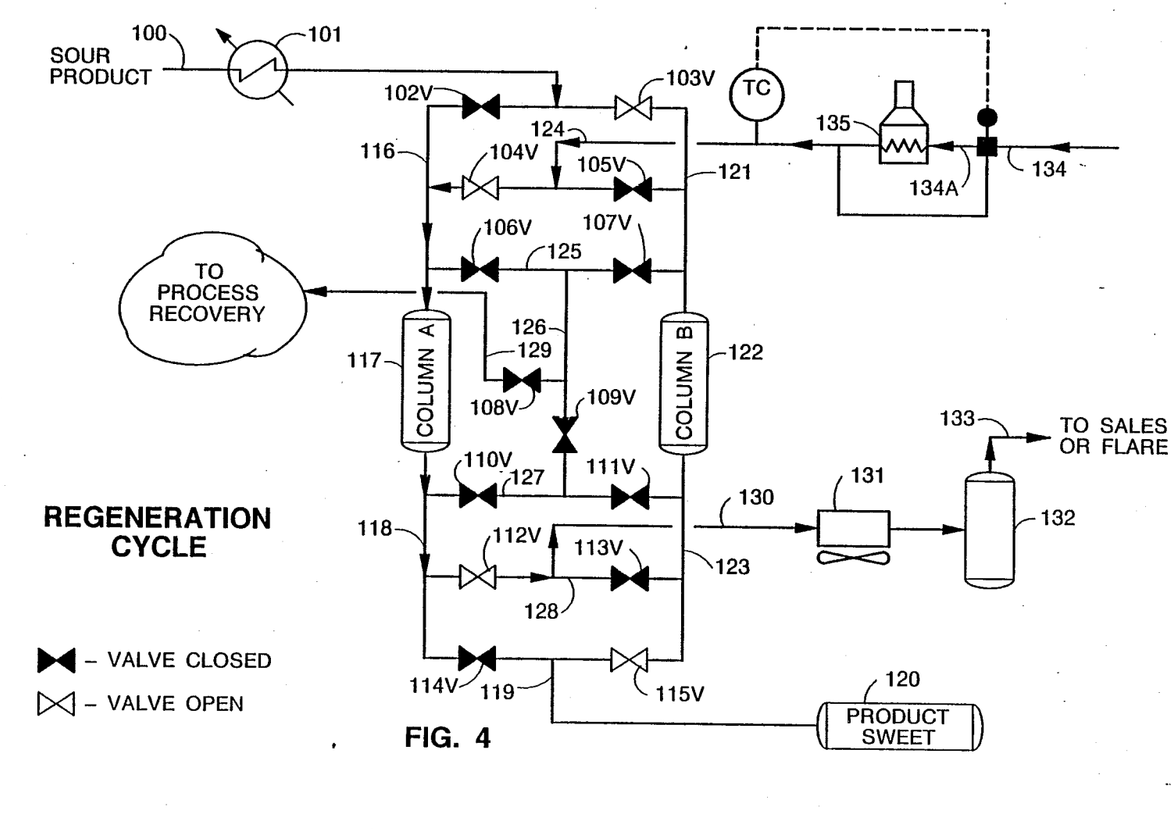

FIG. 4: In the regeneration cycle, the purge fluid is heated in unit 135 to a temperature sufficient to desorb and to vaporize any sulfur compounds and residual sponged hydrocarbon product remaining on the molecular sieves in Column A. The vaporous effluent passing through Column A is cooled and sent to sales or to the flare or to an amine treating plant through lines 130 and 133.

Figure 5:
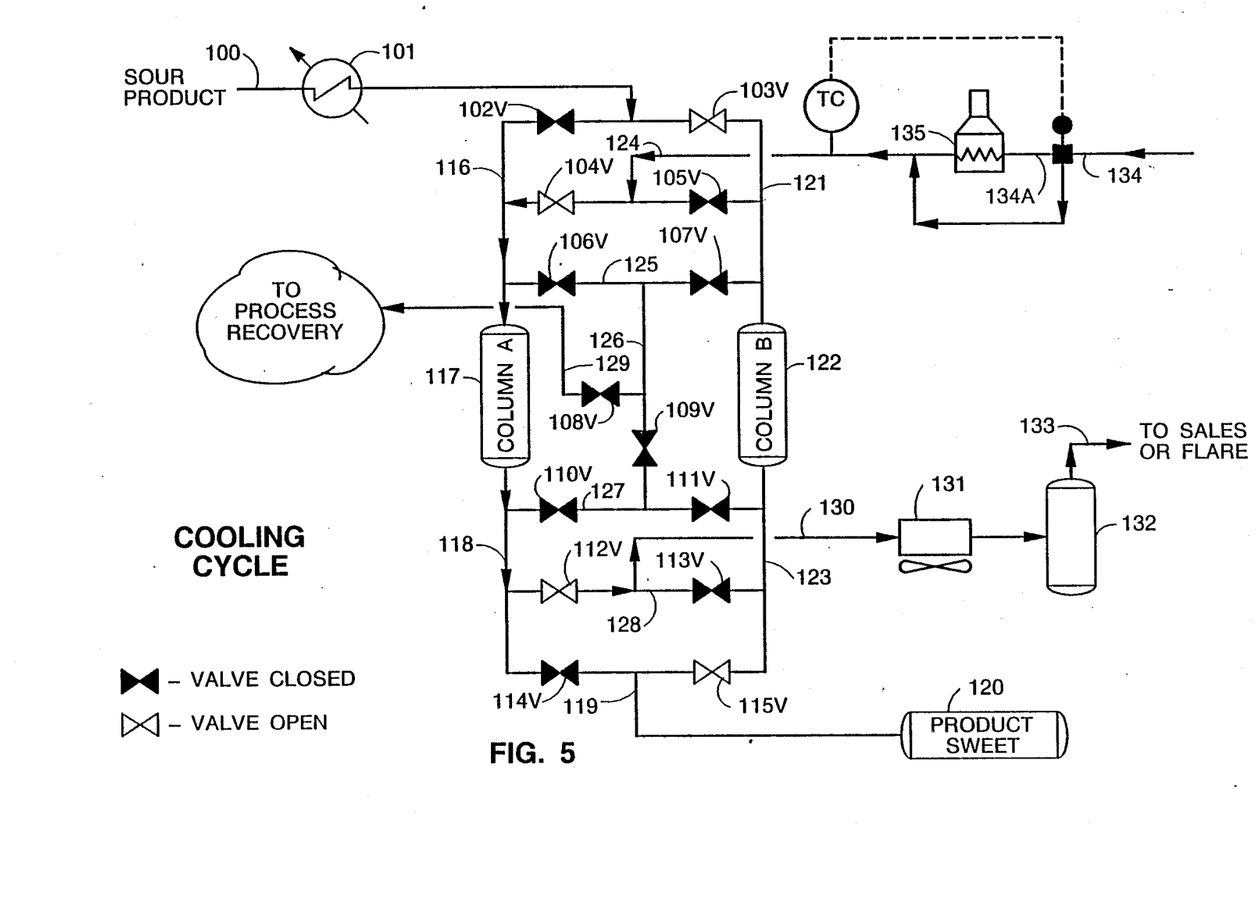

FIG. 5: After the molecular sieves have been regenerated by vaporizing the sorbed compounds, the molecular sieves are cooled by passing the hydrocarbon purge gas through the column or by adding sweetened liquid hydrocarbon from column B to column A. The vaporous effluent is sent to sales or to the flare as shown. A sweetened hydrocarbon fluid is preferred as the purge gas and cooling medium for this cycle, and sweetened hydrocarbon product (e.g., from Column B) is most preferred. This latter embodiment is illustrated in FIG. 5. Note that the vaporous effluent in FIG. 5 is returned to the front end of the plant for further process recovery.

Figure 6:
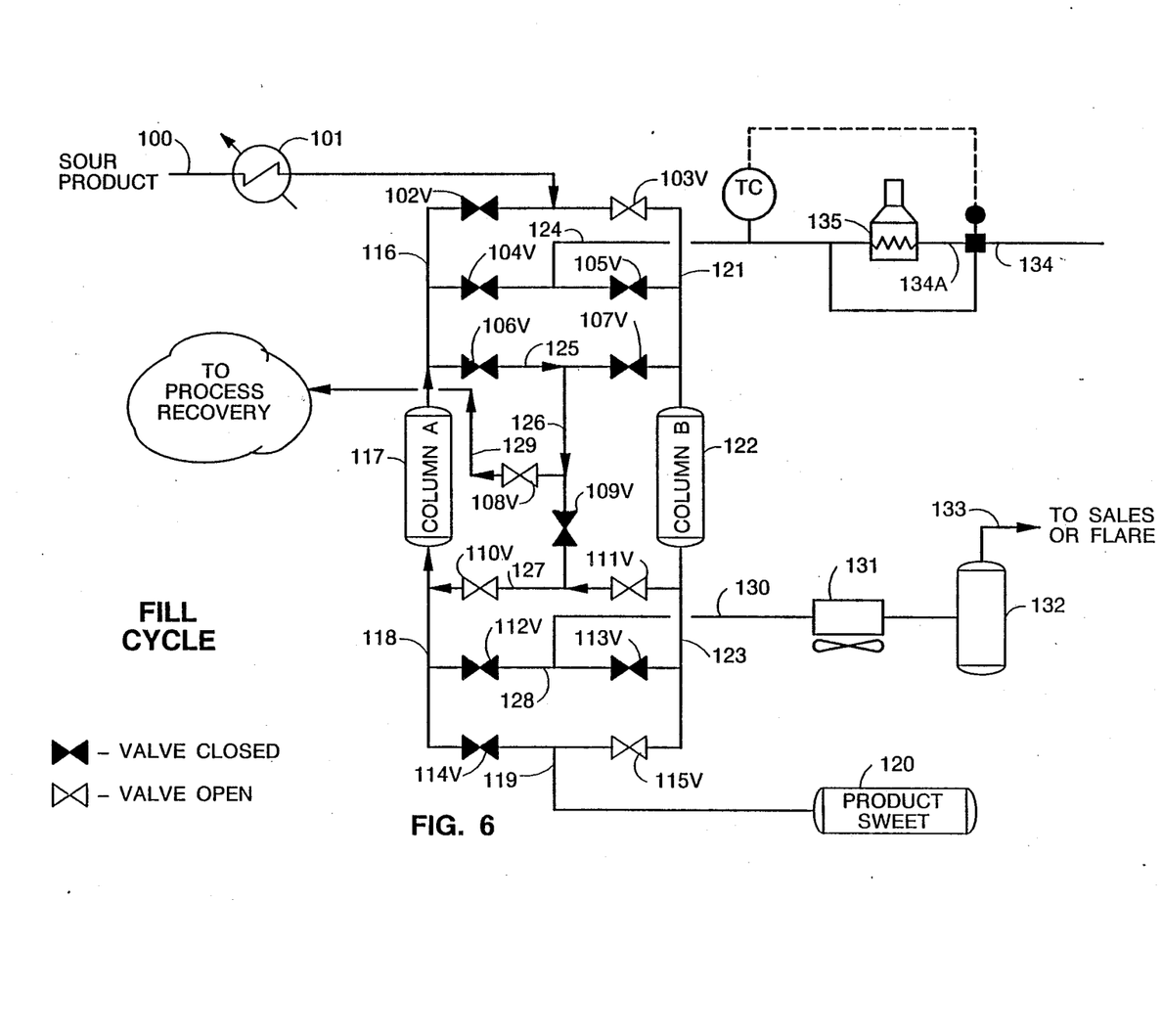

FIG. 6: Column A was then refilled with sweetened liquid hydrocarbon product by diverting the flow of liquid product through line 127 into Column A. Any vaporous effluent is likewise returned to the front end of the plant for further process recovery.

After Column A has been refilled with sweetened liquid hydrocarbon product, the unit is again ready to be placed on sorption and Column B is regenerated in a similar process.

DETAILED DESCRIPTION OF THE INVENTION

As noted above, the molecular sieves that can be used to sorb sulfur species (e.g., COS and $H_2S$) from liquid hydrocarbon streams form a known class of compounds with many members, any one of which can be used in the present invention. The molecular sieves of the crystalline aluminosilicate zeolite type, both naturally occurring and synthetic compositions, are presently preferred because of their commercial availability. The crystalline synthetic zeolites having an average pore diameter of about 5 Angstroms are most preferred. The methods of using such materials to sweeten liquid hydrocarbon streams are well known to those skilled in the art. Generally, the method of choice involves flowing the hydrocarbon stream, under pressure, through a packed bed or column of the molecular sieves under conditions (e.g., flow rate) sufficient for sulfur compounds to be removed by the molecular sieves. Other methods, such as a batch process, could be used but they tend to be less cost effective for treating large volumes of sour hydrocarbon.

The following experimental field trial is conducted in a hydrocarbon treatment plant where the sour propane stream alone is 7,600 barrels per day (BPD). The generally preferred continuous type of operation illustrated in FIGS. 1-6 is chosen to sweeten the propane stream using a commercial synthetic zeolite, molecular sieve type RK-29 from Union Carbide Corporation, Houston, TX. According to Union Carbide sales literature, RK-29 molecular sieves are a Type A crystalline zeolite alkali metal aluminosilicate material having:

(a) a nominal pore size of 3.6 to 4.4 Angstroms,
(b) a bulk density of 41 pounds per cubic foot,
(c) a heat capacity of 0.23 British Thermal Units (BTU) per pound at 10° F.,
(d) a heat of adsorption of 1800 maximum BTU per
(e) a water equilibrium capacity of 21, and pound of water,
(f) a particle size and shape of 1/16 inch pellet. In this trial, the sulfur species in the propane is primarily carbonyl sulfide (COS), with trace amounts of hydrogen sulfide. The sour propane stream flows through two columns connected in parallel and packed with RK-29 molecular sieves.

Each of Column A and B is loaded with the following sequence of materials:

3" Layer of ½-inch Diameter Inert Supports
3" Layer of ¼-inch Diameter Inert Supports
3" Layer of ⅛-inch Diameter Inert Supports 90,000 pounds Molecular Sieve Type RK-29
Floating 20-mesh Stainless Steel Screen
3" Layer of ½-inch Diameter Inert Hold Down Balls
3" Layer of ¼-inch Diameter Inert Hold Down Balls The column outage measurement, from top of final layer of ¼-inch hold down balls to face of top manway flange, is 7.6 feet. The distance from top of the ¼-inch hold down balls to distributor is 3-½ to 4 feet.

The sour propane is then sweetened by flow through Column A, and then through Column B when the molecular sieves in Column A are loaded with sulfur compounds.

At inlet conditions of 600 PPM(V) COS, 80° F. and 7,600 BPD, the predicted COS breakthrough time to 2 PPM(V) is about 16 hours. These are understood to be the worst case conditions which can be reasonably expected for the inlet propane.

The COS adsorption capacity is consistent with predicted performance. Each bed provides a 20-hour breakthrough time to 2 PPM(V) COS at average inlet conditions of 320 PPM(V) COS, 72° F. and 7,600 BPD. Tables 1 and 2 provide the COS adsorption performance measurements.

TABLE 1

Propane Treater - Bed A Adsorption

| CLOCK TIME | COS ANALYSES PPM (V) FEED | OUTLET | REMARKS |
|---|---|---|---|
| 7:30 am | — | — | "A" Starts Adsorption (Day 1) |
| 10:50 am | 310 | — | |
| 11:03 am | — | 1.9 | Inlet Temperature: 74° F. |
| 12:03 pm | 310 | — | |
| 12:20 pm | — | 1.4 | Inlet Temperature: 69° F. |
| 12:40 pm | 220 | 1.3 | Inlet Temperature: 79° F. |
| 1:02 pm | 210 | 1.6 | Inlet Temperature: 71° F. |
| 2:14 pm | 460 | 1.4 | Inlet Temperature: 73° F. |
| 2:56 pm | 490 | 1.0 | Inlet Temperature: 74° F. |
| 3:25 pm | 450 | 0.9 | Inlet Temperature: 75° F. |
| 4:15 pm | 390 | — | |
| 4:24 pm | — | 1.1 | Inlet Temperature: 77° F. |
| 4:42 pm | 490 | 0.8 | Inlet Temperature: 73° F. |
| 5:08 pm | 385 | 0.8 | Inlet Temperature: 75° F. |
| 5:32 pm | 395 | 0.9 | Inlet Temperature: 80° F. |
| 6:10 pm | 370 | 0.9 | Inlet Temperature: 73° F. |
| 7:01 pm | 340 | 0.9 | Inlet Temperature: 71° F. |
| 7:34 pm | 320 | 0.8 | Inlet Temperature: 71° F. |
| 8:05 pm | 380 | 0.7 | Inlet Temperature: 70° F. |
| 8:34 pm | 330 | 0.7 | Inlet Temperature: 70° F. |
| 9:35 pm | 290 | 0.7 | Inlet Temperature: 70° F. |
| 10:32 pm | 300 | 0.6 | Inlet Temperature: 70° F. |
| 11:25 pm | 290 | n.d. | Inlet Temperature: 70° F. |
| 11:59 pm | 230 | n.d. | Inlet Temperature: 70° F. |
| 12:33 am | 240 | n.d. | Inlet Temperature: 70° F. |
| 1:04 am | 260 | n.d. | Inlet Temperature: 70° F. |
| 1:32 am | 245 | n.d. | Inlet Temperature: 71° F. |
| 2:02 am | 230 | n.d. | Inlet Temperature: 71° F. |
| 2:32 am | 235 | n.d. | Inlet Temperature: 70° F. |
| 3:05 am | 245 | 0.8 | Inlet Temperature: 70° F. |
| 3:31 am | 240 | 1.4 | Inlet Temperature: 71° F. |
| 3:55 am | 255 | 2.3 | Inlet Temperature: 70° F. |
| 4:14 am | 260 | 3.5 | Inlet Temperature: 71° F. |
| 4:34 am | 265 | 5.2 | Inlet Temperature: 71° F. |
| 4:53 am | 275 | 8.5 | Inlet Temperature: 71° F. |
| 5:14 am | 260 | 14 | Inlet Temperature: 71° F. |
| 5:32 am | 260 | 17 | Inlet Temperature: 71° F. |
| 6:00 am | 245 | 33 | Inlet Temperature: 71° F. |
| 6:31 am | 240 | 39 | |
| 7:02 am | 250 | 63 | Inlet Temperature: 71° F. |
| 7:32 am | 240 | 88 | |
| 8:00 am | 245 | 95 | Inlet Temperature: 71° F. |
| 8:31 am | 220 | 135 | Inlet Temperature: 71° F. |
| 9:00 am | 215 | 160 | Inlet Temperature: 75° F. |
| 9:10 am | — | — | "A" Ends Adsorption (Day 2) |

TABLE 2

Propane Treater - Bed B Adsorption

| CLOCK TIME | SAMPLE LOCATION | ANALYSES PPM (V) COS | H2S | REMARKS |
|---|---|---|---|---|
| 11:30 pm | Day 5 | — | — | "B" Starts Adsorption |
| 10:45 am | C3-Feed (Day 6) | 320 | — | |
| 10:50 am | Inlet Gas | — | 170 | |
| 10:55 am | B-Top Probe | 17 | — | Inlet Temperature = 71° F. |
| 11:25 am | C3-Feed | 350 | — | |
| 11:36 am | B-Outlet | n.d. | — | |
| 11:47 am | B-Bottom Probe | n.d. | — | |
| 12:09 pm | C3-Feed | 370 | — | |
| 12:15 pm | B-Bottom Probe | n.d. | — | |
| 12:17 pm | B-Outlet | n.d. | — | |
| 12:54 pm | B-Bottom Probe | n.d. | — | Inlet Temperature = 72° F. |
| 1:10 pm | C3-Feed | 490 | — | |
| 1:20 pm | B-Outlet | n.d. | — | |
| 1:24 pm | B-Bottom Probe | 1.5 | — | |
| 1:35 pm | C3-Feed | 375 | — | |
| 1:42 pm | B-Bottom Probe | 6 | — | |
| 1:45 pm | B-Bottom Probe | n.d. | — | |
| 2:08 pm | B-Bottom Probe | 1.5 | — | Inlet Temperature = 73° F. |
| 2:25 pm | B-Bottom Probe | 1.5 | — | Inlet Temperature = 72° F. |
| 2:38 pm | B-Outlet | n.d. | — | |
| 2:44 pm | B-Bottom Probe | n.d. | — | Inlet Temperature = 72° F. |
| 2:30 pm | C3-Feed | 470 | — | |
| 3:05 pm | C3-Feed | 460 | — | |
| 3:13 pm | B-Outlet | n.d. | — | |
| 3:21 pm | B-Bottom Probe | 2.0 | — | Inlet Temperature = 73° F. |
| 3:40 pm | B-Outlet | n.d. | — | Inlet Temperature = 73° F. |
| 3:45 pm | C3-Feed | 480 | — | |
| 3:56 pm | B-Outlet | n.d. | — | Inlet Temperature = 75° F. |
| 4:00 pm | C3-Feed | 450 | — | |
| 4:10 pm | B-Outlet | n.d. | — | Inlet Temperature = 73° F. |
| 4:14 pm | C3-Feed | 460 | — | |
| 4:30 pm | B-Outlet | n.d. | — | |
| 4:34 pm | C3-Feed | 520 | — | |
| 4:54 pm | C3-Feed | 530 | — | |
| 4:57 pm | B-Outlet | n.d. | — | Inlet Temperature = 72° F. |
| 5:32 pm | C3-Feed | 480 | — | |
| 5:35 pm | B-Outlet | n.d. | — | Inlet Temperature = 73° F. |
| 6:02 pm | C3-Feed | 470 | — | |
| 6:05 pm | B-Outlet | n.d. | — | Inlet Temperature = 72° F. |
| 6:32 pm | C3-Feed | 400 | — | |
| 6:35 pm | B-Outlet | n.d. | — | Inlet Temperature = 72° F. |
| 7:05 pm | C3-Feed | 350 | — | |
| 7:07 pm | B-Outlet | 1.4 | — | Inlet Temperature = 72° F. |
| 7:23 pm | B-Outlet | 1.7 | — | Inlet Temperature = 72° F. |
| 7:39 pm | B-Outlet | 1.5 | — | Inlet Temperature = 72° F. |
| 7:40 pm | Bed Switch | — | — | "A" Starts Adsorption |

Column A was regenerated in several steps: First, the flow of sour propane was diverted from Column A to Column B. Column A was then drained by flowing residue gas (135° F.; 330 psig; 1MMSCFD) through the column until the low level switch in the column was satisfied and passing the effluent to Column B, per FIG. 2. Column A was then gas (550° to 600° F.; 330 psig; million standard cubic feet per day, 4 MMSCFD) through the column for 1.5 to 4.5 hours and passing the effluent back to the front end of the hydrocarbon recovery plant where the sponged propane and residue gas were recombined with hydrocarbon feed, per FIG. 3. Next, the molecular sieves in Column A were regenerated by flowing hot residue gas (600° F.; 385 psig; 16 MMSCFD) through the column for 3 to 4.5 hours and passing the effluent to the flares or sweetening plant, per FIG. 4. The molecular sieves were then cooled by flowing residue gas or sweetened liquid propane through Column A and the effluent was discharged to the flare or a sweeten plant or hydrocarbon recovery plant, per FIG. 5. Column A was then refilled with sweetened propane (when cooled with residue gas) and the effluent was passed to the front end of the hydrocarbon recovery plant for further recovery of the propane vapors which formed as the liquid propane cools the molecular sieves to a temperature below the boiling point of propane, at operating pressure, so that the column can be put back onto adsorption mode, per FIG. 6.

In the purge step, a substantial amount of sponged propane (about 50 percent) was removed/recovered by flowing the purged gas through the column for only 1.5 hours at 200° F. at a flow rate of 4 MMSCFD. This recovery was increased to virtually 100 percent by changing the temperature to 600° F. and maintaining the flow for 4.5 hours at a flow rate of 4MMSCFD. COS breakthrough during the propane purge step occurs simultaneously with a precipitous drop in the propane concentration in the effluent gas, signalling the removal of virtually all the propane from the bed of molecular sieves.

To summarize this field trial experiment:

Both molecular sieve beds provided a predictable performance of 20 hours to 2 PPM(V) COS breakthrough an average inlet conditions of 320 PPM(V) COS, 72° F. and a propane throughput of 7,600 BPD;

The predicted breakthrough time to 2 PPM(V) COS at inlet conditions of 600 PPM(V) COS, 80° F. and 7,600 BPD was about 16 hours;

The propane purge step of 1.5 hours at 200° F. with 4 MMSCFD, allowed for recovery of approximately 50 percent of the total propane remaining on the bed following the drain step;

Field optimization of the propane purge step consisting of changing the temperature to 600° F. and the step time to 4.5 hours at 4 MMSCFD, allowed for recovery of virtually 100 percent of the total propane remaining on the bed following the drain step;

The regeneration step is consistent with predictions with respect to the measured $H_2S$ and COS desorption profiles, and is subject to optimization.

Column A performed as expected in sweetening the propane when the feed stream was diverted from Column B to Column A. Column B was then regenerated in a similar manner and with similar results.

What is claimed is:

1. A molecular sieve regenerating process comprising the steps of:
    (a) stopping the flow of sour liquid hydrocarbon to a bed of molecular sieves in a hydrocarbon sorbtion plant,
    (b) draining liquid hydrocarbon from the bed of molecular sieves,
    (c) purging the bed with a heated gaseous hydrocarbon until substantial amounts of sponged hydrocarbon has been removed from the bed,
    (d) regenerating the purged bed by contact with a gaseous hydrocarbon heated to a temperature sufficient to volatilize and desorb sulfur species from the molecular sieves, and
    (e) cooling the regenerated bed.

* * * * *

UNITED STATES PATENT AND TRADEMARK OFFICE
CERTIFICATE OF CORRECTION

PATENT NO. : 4,935,400

DATED : June 19, 1990

INVENTOR(S) : BLACKBURN, ET AL

It is certified that error appears in the above--identified patent and that said Letters Patent is hereby corrected as shown below:

Column 2, line 60, after "steps" insert --of:--.

Column 4, line 55, after "per" insert --pound of water--.

Column 6, line 65, after "was then" insert --purged to remove sponged propane by flowing heated residue--.

Column 6, line 65, after "psig;" insert --4--.

Signed and Sealed this

Seventeenth Day of March, 1992

*Attest:*

HARRY F. MANBECK, JR.

*Attesting Officer*          *Commissioner of Patents and Trademarks*